United States Patent
McGovern et al.

(10) Patent No.: US 6,692,493 B2
(45) Date of Patent: *Feb. 17, 2004

(54) METHOD FOR PERFORMING INTRAURETHRAL RADIO-FREQUENCY URETHRAL ENLARGEMENT

(75) Inventors: Francis J. McGovern, Lexington, MA (US); S. Nahum Goldberg, Brookline, MA (US); Eric R. Cosman, Belmont, MA (US); William J. Rittman, III, Lynnfield, MA (US)

(73) Assignees: Cosman Company, Inc., Belmont, MA (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/227,533

(22) Filed: Aug. 26, 2002

(65) Prior Publication Data

US 2003/0060819 A1 Mar. 27, 2003

Related U.S. Application Data

(63) Continuation of application No. 09/021,802, filed on Feb. 11, 1998, now Pat. No. 6,440,127.

(51) Int. Cl.[7] ............................................... A61B 18/14
(52) U.S. Cl. ........................... 606/41; 607/99; 607/113
(58) Field of Search ............................. 606/41, 49, 50; 607/98, 99, 105, 113

(56) References Cited

U.S. PATENT DOCUMENTS

| | | | |
|---|---|---|---|
| 2,407,690 A | 9/1946 | Southworth | 128/422 |
| 4,116,198 A | 9/1978 | Roos | 128/303.15 |
| 4,184,492 A | 1/1980 | Meinke et al. | 128/303.14 |
| 4,411,266 A | 10/1983 | Cosman | 128/303.18 |

(List continued on next page.)

FOREIGN PATENT DOCUMENTS

| | | | |
|---|---|---|---|
| EP | 0 754 437 A2 | 1/1997 | A61B/17/39 |
| WO | WO 91/13650 | 9/1991 | A61N/5/04 |
| WO | WO 96-00036 | 1/1996 | |
| WO | WO 96-00039 | 1/1996 | |
| WO | WO 96/34571 | 11/1996 | |
| WO | WO 96/37158 | 11/1996 | A61B/17/36 |
| WO | WO 97/00646 | 1/1997 | A61B/17/39 |
| WO | WO 97/00647 | 1/1997 | A61B/17/39 |
| WO | WO 97/28840 | 8/1997 | A61M/25/10 |

OTHER PUBLICATIONS

US 5,326,343, 7/1994, Rudie et al. (withdrawn)
Djavan, et al. "Minimally Invasive Procedures and Medical Management—Their Relative Merits in Treating Lower Urinary Tract Symptoms of Benign Prostatic Hyperplasia", Reviews in Urology, 2:105–114 (2000).

(List continued on next page.)

*Primary Examiner*—Lee Cohen
(74) *Attorney, Agent, or Firm*—Fish & Richardson P.C.

(57) ABSTRACT

Relief of urethral obstruction is achieved by heat ablation of prostatic tissue by an ablation electrode passed within the urethra to a position in the prostate near the point of urethral obstruction. The electrode is coupled to a high frequency power supply to ablatively heat the urethra and the prostatic tissue near the urethra. Image guidance of the electrode placement is monitored by an imaging device. The temperature of the tissue is sensed at the electrode to control the high frequency heating energy and ablation process. The electrode has a blunt tip to help prevent piercing of the wall of the urethra during insertion of the electrode into the urethra through the penis and the positioning of the electrode tip near to the point of urethral obstruction. Several forms of electrodes, apparatus, and methods accommodate the specific objectives.

34 Claims, 6 Drawing Sheets

U.S. PATENT DOCUMENTS

| | | | | |
|---|---|---|---|---|
| 4,682,596 | A | 7/1987 | Bales et al. | 128/303.14 |
| 4,785,823 | A | 11/1988 | Eggers et al. | |
| 4,966,597 | A | 10/1990 | Cosman | |
| 4,967,765 | A | 11/1990 | Turner et al. | 128/785 |
| 4,979,948 | A | 12/1990 | Geddes et al. | 606/33 |
| 5,007,437 | A | 4/1991 | Sterzer | 428/786 |
| 5,061,266 | A | 10/1991 | Hakky | 606/15 |
| 5,112,330 | A | 5/1992 | Nishigaki et al. | 606/46 |
| 5,178,620 | A | 1/1993 | Eggers et al. | 606/41 |
| 5,220,927 | A | 6/1993 | Astrahan et al. | 128/785 |
| 5,249,585 | A | 10/1993 | Turner et al. | |
| 5,257,977 | A | 11/1993 | Eshel | |
| 5,263,931 | A | 11/1993 | Miller | |
| 5,277,201 | A | 1/1994 | Stern | 607/98 |
| 5,300,099 | A | 4/1994 | Rudie | 607/101 |
| 5,301,687 | A | 4/1994 | Wong et al. | 606/41 |
| 5,304,214 | A | 4/1994 | DeFord et al. | 607/105 |
| 5,322,507 | A | 6/1994 | Costello et al. | 128/4 |
| 5,330,518 | A | 7/1994 | Neilson et al. | 607/101 |
| 5,348,554 | A | 9/1994 | Imran et al. | 606/41 |
| 5,370,675 | A | 12/1994 | Edwards et al. | 607/101 |
| 5,370,677 | A | 12/1994 | Rudie et al. | 607/101 |
| 5,403,311 | A | 4/1995 | Abele et al. | 606/49 |
| 5,454,809 | A | 10/1995 | Janssen | 606/41 |
| 5,464,437 | A | 11/1995 | Reid et al. | 607/101 |
| 5,472,441 | A | 12/1995 | Edwards et al. | |
| 5,480,417 | A | 1/1996 | Hascoet et al. | |
| 5,486,161 | A | 1/1996 | Lax et al. | 604/22 |
| 5,492,529 | A | 2/1996 | Neuwirth et al. | |
| 5,509,929 | A | 4/1996 | Hascoet et al. | 607/101 |
| 5,520,684 | A | 5/1996 | Imran | |
| 5,542,915 | A | 8/1996 | Edwards et al. | 604/22 |
| 5,545,137 | A | 8/1996 | Rudie et al. | 604/96 |
| 5,545,161 | A | 8/1996 | Imran | |
| 5,599,294 | A | 2/1997 | Edwards et al. | 604/22 |
| 5,599,346 | A | 2/1997 | Edwards et al. | 606/41 |
| 5,620,480 | A | 4/1997 | Rudie | 607/101 |
| 5,628,770 | A | 5/1997 | Thome et al. | 607/101 |
| 5,630,426 | A | 5/1997 | Eggers et al. | |
| 5,645,528 | A | 7/1997 | Thome | 604/96 |
| 5,681,282 | A | 10/1997 | Eggers et al. | |
| 5,697,909 | A | 12/1997 | Eggers et al. | 604/114 |
| 5,733,315 | A | 3/1998 | Burdette et al. | 607/97 |
| 5,733,316 | A | 3/1998 | Tierney et al. | 607/101 |
| 5,755,754 | A | 5/1998 | Rudie et al. | |
| 5,810,764 | A | 9/1998 | Eggers et al. | 604/23 |
| 5,849,011 | A | 12/1998 | Jones et al. | |
| 5,891,134 | A | 4/1999 | Goble et al. | 606/27 |
| 5,944,715 | A | 8/1999 | Goble et al. | 606/41 |
| 6,171,306 | B1 | 1/2001 | Swanson et al. | |
| 6,440,127 | B2 * | 8/2002 | McGovern et al. | 606/41 |

OTHER PUBLICATIONS

Thermex Clinical Data, Direx Medical Systems, Nov. 1993.

Turapy Clinical Data, Direx Medical Systems, undated.

Bhanot, et al. "A Radiofrequency Method of Thermal Tissue for Benign Prostatic Hyperplasia," *Urology*, Mar. 1995, 45:427–433.

Cosman, et al. " Theoretical Aspects of Radiofrequency Lesions in the Dorsal Root Entry Zone," *Neurosurgery*, 15:945–950 (1984).

Dawkins, et al., "Radiofrequency heat–treatment to the prostate for bladder outlet obstruction associated with benign prostatic hyperplasia: a 4–year outcome study," *British Journal of Urology*, 79:910–914 (1997).

Brochure, SMK Sluijter–Mehta Kits, "The Finest Radiofrequency Electrodes for Pain Therapy" Radionics, Burlington, MA, 1996.

Blute, Michael L., et al., "Transurethral Microwave Thermotherapy for Management of Benign Prostatic Hyperplasia: Results of the United States Prostatron Cooperative Study," *Journal of Urology*; Nov. 1993; vol. 150, No. 5, Part 2 of 2; pp 1591–1596.

Cosman et al., "Theoretical Aspects of Radiofrequency Lesions in the Dorsal Root Entry Zone" *Neurosurgery*, vol. 15, No. 6, 945–950, Dec. 1984.

Costello et al., "Nd:YAG Laser Ablation of the Prostate as a Treatment for Benign Prostatic Hypertrophy" *Lasers in Surgery and Medicine*, vol. 12, No. 2; pp121–124; 1992.

Goldberg et al., "Tissue Ablation with Radiofrequency: Effect of Probe Size, Gauge, Duration, and Temperature on Lesion Volume" *Acad. Radiol.*, vol. 2, No. 5 399–404, May 1995.

Goldberg, Nahum S., et al., "Hepatic Metastases: Percutaneous Radio–Frequency Ablation with Cooled–Tip Electrodes," *Radiology*; Nov. 1997; vol. 205, No. 2; pp 367–373.

Goldwaser, B., et al., "Transurethral Needle Ablation (TUNA) of the Prostate Using Low–Level Radiofrequency Energy: An Animal Experimental Study," *European Urology*; Oct. 1993; vol. 24; pp 400–405.

Harada et al., "Microwave Surgical Treatment of Diseases of Prostate" *Urology*, vol. XXVI, No. 6, 572–576, Dec. 1985.

Kramolowsky, et al, "The Urological Application of Electrosurgery," *The Journal of Urology*, vol. 146, 669–674, Sep. 1991.

Kramolowsky, et al, "Use of 5f Bipolar Electrosurgical Probe in Endoscopic Urological Procedures," *The Journal of Urology*, vol. 143, 275–277, Feb. 1990.

McGahan et al., "Percutaneous Ultrasound–Guided Radiofrequency Electrocautery Ablation of Prostate Tissue in Dogs" *Acad Radiol.*; vol. 2, No. 1; pp 61–65, Jan. 1995.

Nardella, "Radio Frequency Energy and Impedance Feedback," *SPIE*, vol. 1068; pp. 42–48, (1989).

Onik et al., "Transrectal Ultrasound–Guided Percutaneous Radical Cryosurgical Ablation of the Prostate," *Cancer*; Aug, 15, 1993; vol. 72, No. 4; pp 1291–1299.

*Radionics Neurosurgical Instruments*, Trigeminal Neralgia Kit Description, (1981).

Schulman, Claude C., et al., "Transurethral Needle Ablation (TUNA): Safety, Feasibility, and Tolerance of a New Office Procedure for Treatment of Benign Prostatic Hyperplasia," *European Urology*; vol. 24; pp 415–423; 1993.

Sunshine, Robert D., M.D., et al., "Complications of Transurethral Resection of the Prostate," *Urologic Complications, Medical and Surgical, Adult and Pediatric*, 1986; Chapter 18; pp 231–246.

Tucker, et al, "A Comparison of Urologic Application of Bipolar Versus Monopolar Five French Electrosurgical Probes," *The Journal of Urology*, vol. 141, 662–665, Mar., 1989.

* cited by examiner

METHOD FOR PERFORMING INTRAURETHRAL RADIO-FREQUENCY URETHRAL ENLARGEMENT

This application is a continuation of U.S. application Ser. No. 09/021,802, filed Feb. 11, 1998, now U.S. Pat. No. 6,440,127.

FIELD OF THE INVENTION

This invention relates generally to advances in medical systems and procedures for prolonging or improving human life. More particularly, this invention relates to an improved method and system for alleviating urinary obstruction caused by enlargement of the prostate by performing intraurethral radio-frequency ablation for urethral enlargement.

BACKGROUND OF THE INVENTION

A majority of all males over 60 years old experience partial or complete urinary obstruction because of enlargement of the prostate. This condition usually originates from benign prostatic hyperplasia (BPH), which is an increase in cell mass near the urethra, or less likely, from prostate cancer. Both these conditions involve an increase in prostatic tissue mass, which in its increased state encroaches on the urethra and obstructs the urinary pathway.

In the case where urinary obstruction is caused by BPH, a common treatment involves a medical procedure using a medical side-cutting instrument and/or endoscope to surgically enlarge a passageway for urine flow through the prostate. The side-cutting instrument or endoscope is passed through the penis into the urethra and is surgically used to remove prostate tissue and part of the urethra at the point of obstruction. This procedure is referred to as "Trans-Urethral Resection of the Prostate" (or "TURP"). This procedure, although effective, is invasive and complicated. For example, it requires the use of anesthesia and substantial hospital care. It also has the risk of causing bleeding. Moreover, it is expensive and causes great discomfort and trauma to the patient. For example, chapter 18, entitled "Complications of Transurethral Resection of the Prostate," by R. Sunshine and M. Droller, of a book entitled *Urologic Complications, Medical and Surgical, Adult and Pediatric,* edited by Fray S. Marshall (Yearbook Medical Publishers, 1986), elaborates on the various complications of the TURP procedure.

In the case where urinary obstruction results from prostatic cancer, surgical prostatectomies are commonly used to eliminate the obstruction. However, surgical prostatectomies have serious side effects and risks, including impotence and urinary incontinence.

In recent years, less invasive systems and procedures that inflict less trauma on patients have been attempted. One such procedure, called "Trans-Urethral Needle Ablation" (or "TUNA"), involves passing a radio-frequency (RF) instrument such as a catheter, cannula, sheath, or scope into the urethra. The RF instrument houses special RF electrode tips that emerge from the side of the instrument. The tips are pushed out of the instrument along off-axis paths to pierce the urethral wall and pass into the prostatic tissue outside of the urethra. As a result of the various electrodes emerging from the side of the instrument, such radio-frequency instruments are frequently complex and expensive. By heating the prostate with RF power applied through the electrode tips emerging from the side of the radio-frequency (RF) instrument, the prostate tissue surrounding the urethra is ablated. Specifically, heat ablation is performed at multiple locations outside the urethra to provide a series of ablations, thereby causing the prostate tissue outside the urethra to die and necrose. Subsequent to heating, the necrotic tissue is absorbed by the body or excreted, thereby reducing the tissue mass outside the urethra, which consequently reduces the urethral obstruction. For further explanation of this system and procedure, one can consult a research paper published by Goldwasser, et al., entitled "Transurethral needle ablation (TUNA) of the prostate using low-level radio-frequency energy: an animal experimental study;" *Eur. Urol.,* vol. 24, pp. 400–405 (1993); and a research paper published by Schulman, et al., entitled "Transurethral needle ablation (TUNA); safety, feasibility, and tolerance of a new office procedure for treatment of benign prostate hyperplasia;" *Eur. Urol.,* vol. 24, pp. 415–423 (1993). Also, product literature on the TUNA system available from a company named Vitamed, Inc., of Menlo Park, Calif., carries some description of the procedure.

The TUNA system and procedure is generally used to relieve urethral obstruction caused by BPH. It favors a transurethral approach because the target tissue to be ablated is generally near to it. However, again, although the TUNA system and procedure is effective, it requires epidural or general anesthetic, and generally causes the patient great discomfort and pain. Moreover, the TUNA procedure is medically and technically very complex for surgeons to perform, requiring a complicated and expensive catheter or sheath or RF electrode system to perform it. Also, it is a relatively blind procedure in the sense that the ends of the RF electrodes emerging at the side of the radio-frequency electrode system, once they penetrate the target tissue cannot be seen. Nor is there any technique for providing a visual representation of them. Furthermore, the TUNA system and procedure attempts to leave the urethra intact and uninjured by the application of RF heating, which is difficult to achieve, making its outcome uncertain. The TUNA system and procedure causes scratching of the urethra, bleeding or irritation from a cystoscope, cannula, catheter, or tissue-piercing electrode tips passed into the urethra. Furthermore, the TUNA procedure produces trapped coagulated and necrotic tissue or fluid in the interstitial region of the prostate outside the urethra. This can result in swelling and increased pressure of tissue outside the prostate as the necrotic tissue is absorbed by the body. Such pressure can compress the urethra to further enhance its obstruction.

It is observed that such techniques have not been directed at creating ablation of urethra or the periurethral region (the region surrounding the urethra or the critical prostate region) for the reasons discussed above. Accordingly, it would be desirable to have an effective technique to perform intraurethral RF electrode ablation of the urethra and periurethral tissue for the purposes of alleviating urinary obstruction caused by enlargement of the prostate and that avoids the limitations of the art.

Another system and procedure contemplated by Onik, et al. is described in their research paper entitled "Transrectal ultrasound-guided percutaneous radical cryosurgical ablation of the prostate," *Cancer,* vol. 72, pp. 1291–1299 (1993). This technique is utilized for the treatment of prostate cancer and involves disposing cryogenic (freezing) probes in the prostate for ablating the cancer cells. Onik, et al., propose passing a cryogenic probe transperineally (through the perineum) into the prostate. At the same time, an imaging ultrasonic probe is passed through the rectum and is used to visualize the position of the cryogenic probe and the volume of cryogenic ablation in the prostate. This technique requires use of cryogenic probes (also referred to as cryo-probes)

having a relatively large diameters. The cryo-probes are complex in construction and operation and require elaborate cooling and thawing cycles, making the procedure typically quite complicated and expensive. It is technically challenging and critical to maintain precise temperatures at the target tissue area to prevent hemorrhaging when removing the probe and also to prevent freezing sensitive rectal mucosa tissue.

One more recent procedure contemplated and reported by McGahan, et al., in their research paper entitled "Percutaneous Ultrasound-Guided Radiofrequency Electrocautery Ablation of Prostate Tissue in Dogs," *Acad. Radiol.,* vol. 2, pp. 61–65 (1994), involves placing an RF electrode transrectally into the prostate of a dog under rectal ultrasound guidance. Their intent was solely to explore the feasibility of ablating cancerous tumors within the peripheral region of the prostate. Their research treated only normal animals and no ablation of cancer tissue was actually performed. McGahan, et al., hoped to prevent RF heat ablation of the urethra (which is located centrally in the prostate). To achieve their objective, they suggested that the urethra should be irrigated with saline solution, using a catheter, to prevent RF heat damage to the urethra and periurethral tissue. They concluded that their system and procedure was impractical for ablating prostate cancer cells, because the RF lesions were limited to 1 to 1.5 cm in diameter, which they felt would be too small to adequately treat malignant cancer cells.

Generally, prostate cancer primarily occurs in the peripheral (non-central) zone of the prostate. It is often multi-focal, near the rectal wall, and near nerves controlling potency. Recognizing the restraints and delicate circumstances, McGahan, et al., were discouraged by the results of their research. They concluded that their technique may be applicable to only a small percentage of prostate carcinomas, specifically those that are small and can be imaged by ultrasound. In their paper, they emphasized their concern for preventing RF heat damage to the rectal mucosa tissue. Thus, as a result of their efforts to treat prostate cancer, which is predominantly located in the peripheral non-central part of the prostate, they focused their research efforts on the peripheral, perirectal regions of the prostate. Their research did not contemplate RF ablation in the central periurethral region to produce an ablation cavity near the urethra or to ablate the urethra itself. In fact, they explicitly sought to avoid injury of the urethra by avoiding treatment of periurethral tissues. Their method and objectives were directed to cancer and were found to be disadvantageous for the treatment of BPH or for treating urethral or periurethral tissues by radio-frequency (RF) ablation to relieve urinary obstruction.

It should be recognized that the theory behind and practice of RF heat lesioning has been known for decades, and a wide range of RF generators and electrodes for accomplishing such practice exist. For example, equipment for performing heat lesions is available from Radionics, Inc., located in Burlington, Mass. Radio-frequency (RF) ablation is well known and described in medical and clinical literature. To that end, a research paper by E. R. Cosman, et al., entitled "Theoretical Aspects of Radio-frequency Lesions in the Dorsal Root Entry Zone," *Neurosurgery,* vol. 15; no. 6, pp. 945–950 (1984), describing various techniques associated with radio-frequency lesions, is incorporated herein by reference. Also, a research paper by S. N. Goldberg, et al., entitled "Tissue Ablation with Radio-frequency: Effect of Probe Size, Gauge, Duration, and Temperature on Lesion Volume," *Acad Radiol,* vol. 2; pp. 399–404 (1995), describes techniques and considerations relating to tissue ablation with radio-frequency energy.

In addition, a paper by S. N. Goldberg, et al., entitled "Hepatic Metastases: Percutaneous Radio-Frequency Ablation with Cooled-Tip Electrodes," *Radiology,* vol. 205, n. 2, pp. 367–373 (1997), describes various techniques and considerations relating to tissue ablation with radiofrequency electrodes having cooled electrode tips. Cooled ablation electrodes will maintain tissue near the electrode at lowered temperatures which are below ablation temperatures. Cooling in the urethra by a catheter is suggested by McGahan et al., cited above, to prevent RF heat damage to the urethra and periurethral tissue.

However, for the reasons described above, such techniques have never been performed to ablate the periurethral region and the urethra itself using an intraurethral RF electrode that does not pierce the urethra. Accordingly, an effective technique for performing intraurethral RF electrode ablation to achieve urethral enlargement is desirable for purposes of alleviating urinary obstruction caused by enlargement of the prostate.

SUMMARY OF THE INVENTION

The present invention is directed to a system and procedure for radio-frequency (RF) heat ablation of prostatic tissue through the use of an RF electrode, which is advanced into the urethra through the penis and positioned intraurethrally (within the urethra). The ablation is performed for the treatment of benign prostatic hyperplasia (BPH) and the associated alleviation of urethral obstruction. The system and procedure of the present invention are different from any of the systems and procedures discussed in the background section. The advantages of the present system and method reside in their combined simplicity, economy, control, consistency, enablement of good ablation position and shape, and clinical effectiveness.

As one example, urinary bladder outlet obstruction can be effectively treated using the present system and technique, which is minimally invasive. The technique of the present invention involves inserting an RF electrode into the urethra to the region of urethral obstruction in the prostate. The conductive portion of the RF electrode remains within the urethra. This avoids the more difficult and uncomfortable transurethral approach of the TUNA system procedure discussed above, and may be done without need for passing one or more side-outlet RF electrodes through the urethral wall (via a transurethral approach) into the prostatic tissue surrounding the urethra. In various embodiments, the present system and procedure may include image guidance, which can be performed in any of a variety of ways including ultrasound, CT, MRI, fluoroscopy, X-rays, or other well known imaging techniques. It may include visual guidance accomplished by passing the RF electrode through a cystoscope placed in the urethra.

In accordance with one embodiment of the invention, an RF electrode may be passed through an endoscope or cystoscope that has been inserted in the urethra. The electrode's exposed RF tip emerges from the endoscope and is placed in the prostate, near the portion of the urethra that is being obstructed by the enlarged prostate tissue volume (for example, as occurs in cases of benign prostatic hyperplasia (BPH) and some types of prostatic cancer). The endoscope provides direct visualization of the urethra and the position of the RF electrode tip within it. In a variation of this embodiment, the RF electrode is passed into the urethra without endoscopic guidance. In the latter case, X-ray or ultrasound imaging may be used to determine the position of the electrode.

In contrast to the TUNA technique, the RF electrode of the present invention can be used without piercing the urethra. It enables patients who cannot tolerate the TUNA system and procedure to receive RF ablation treatment. For example, such patients could be those requiring anticoagulation medication for cardiac or neurological problems who should not risk bleeding from a punctured urethra.

The present system and procedure has the further advantage of being able to control the positioning of the electrode by direct endoscopic visualization imaging techniques, reducing the risks associated with the blind TUNA procedure.

In a technique performed according to the present invention, an RF heat lesion is made to ablate the urethra and the periurethral region (i.e., tissue near or on the urethral tube) to induce necrosis of the prostate tissue near the urethra and of the urethra itself This induces a symmetric cavity to be formed via obliteration of the urethra and the central region of the prostate in the patient's body a few days after the procedure is performed. The cavity provides direct communication to and widening of the urethral channel. In accordance with one embodiment of the invention, lesion sizes of 1 to 2 cm diameter can be made, which thereafter induce similarly sized cavities to be formed, thereby enlarging the urethral passage. These exemplary lesion sizes, similar to those made by the TURP procedure, have proven to be adequate to provide relief from BPH.

It should be noted that in contrast to McGahan et al.'s conclusion that such lesion sizes are inadequate for the ablation of prostate carcinomas, the lesion sizes are adequate in treating BPH.

Also, the present technique avoids the need to observe of McGahan et al.'s admonition to avoid heat injury to the urethra, and the corresponding necessity for the irrigation and cooling of the urethra as suggested by the article by McGahan et al. By ablating the urethra itself, the present technique has the added advantage of avoiding the possibility of necrotic tissue and fluid becoming entrapped outside the urethra if the urethra is left intact, as in the case of the TUNA and McGahan et al. procedures.

These features and advantages as well as others of the present method and system will become apparent in the detailed description that follows.

BRIEF DESCRIPTION OF THE DRAWINGS

In the drawings, which constitute a part of the specification, embodiments exhibiting various forms and features hereof are set forth, specifically.

DETAILED DESCRIPTION OF THE INVENTION

Figure 1:
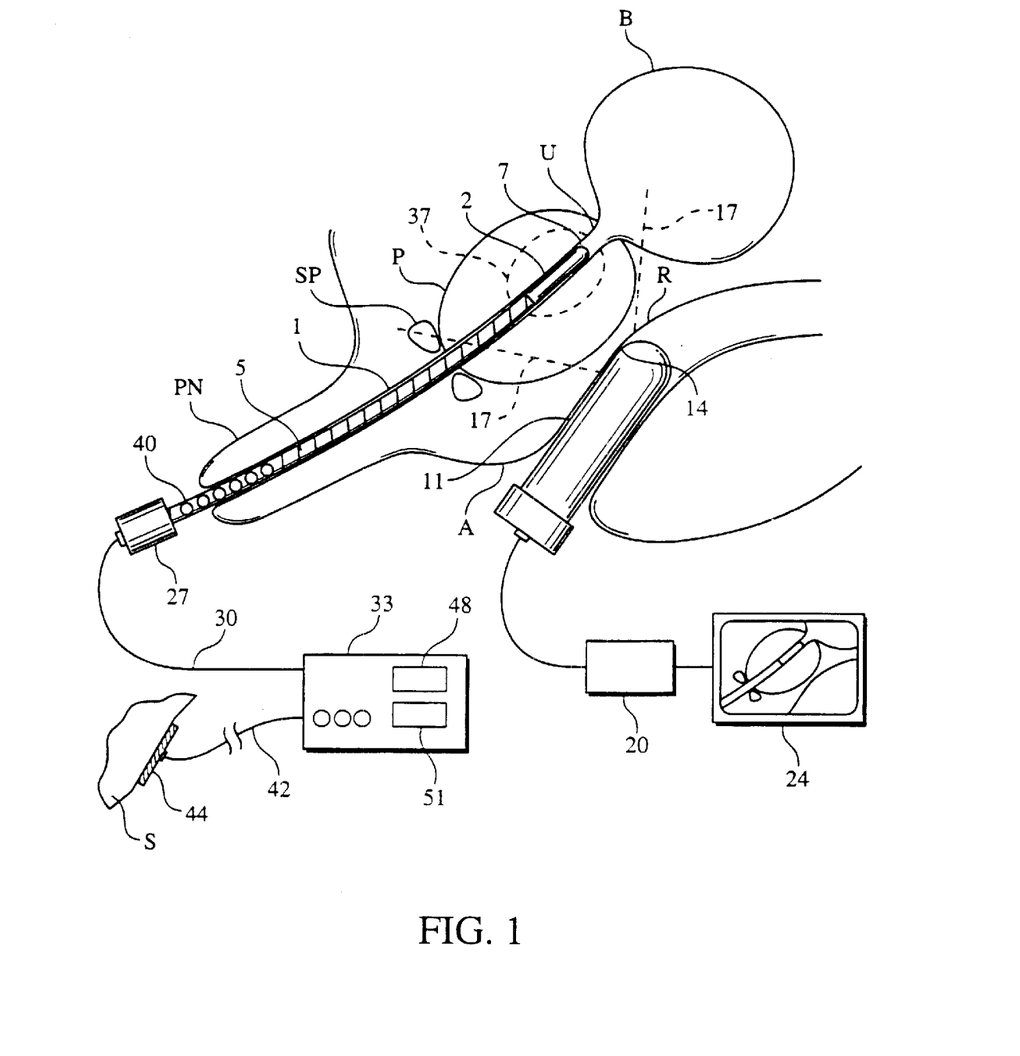
FIG. 1 is a schematic diagram showing a portion of a patient along with a system according to the invention for performing intraurethral radio-frequency (RF) ablation of the urethra and central prostate with ultrasonic imaging guidance.

Referring initially to FIG. 1, in a system in accordance with the present invention, a radio-frequency (RF) electrode 1 is inserted via the penis PN into the urethra U of a living body, such as a patient, and into an operative field within the patient's body, specifically including the prostate gland P. The tip 2 of the electrode 1, which is electrically uninsulated, is placed intraurethrally, within the urethral tube that drains urine from the bladder B in the living body. In the disclosed embodiment of the invention, the electrode 1 has an insulated shaft portion 5, indicated by the hatched area in FIG. 1. The electrode tip 2 preferably has a rounded distal end 7 to facilitate passage through the urethra and into the prostate region without scraping, cutting, or penetrating the urethral wall itself. This configuration of the electrode 1 facilitates the intraurethral approach to placing a radio-frequency (RF) electrode into the prostate.

Also shown in FIG. 1 is an ultrasonic imaging device 11 which is placed intrarectally through the anal opening A. It has an imaging head 14 which rests against the rectal wall R near the prostate P. The ultrasonic imaging device 11 may be any common tool used in diagnostic medicine; such devices are widely available. For example, Accuson, Inc., located in Mountain View, Calif., provides several suitable ultrasonic imaging devices. With the ultrasonic imaging device 11, any desired area of tissue may be imaged. In one embodiment of the invention, the imaging head 14 comprises an ultrasonic scanning transducer.

For example, as illustrated in FIG. 1, the region of tissue falling within the area bounded by the dashed lines 17 is scanned by the ultrasonic scanning transducer 14 to generate a visual image. This image may include the rectal wall R, prostate P, and urethra is U, as well as the electrode 1 and its conductive RF tip 2. The ultrasonic scanning transducer 14 is connected to an ultrasonic image processing unit 20 and a display unit 24, as is common practice. The display unit 24 serves to provide real-time ultrasonic images of the prostate P with the RF electrode tip 2 placed in the urethra U. This way, the guidance provided by the ultrasonic image is used to locate the electrode at an appropriate point of the urethra within the prostate and, if desired, away from particularly sensitive areas such as the apex of the prostate near the sphincter SP.

The radio-frequency electrode 1 has an electrical connection 27 at its proximal end (nearest the surgeon), which is connected by a wire or cable connection 30 to a radiofrequency generator or other high-frequency energy source 33. The radio-frequency generator may be an electrical unit with, for example, a radio-frequency, microwave, or other high frequency power supply that can deliver a high-frequency electrical signal to the electrode tip 2.

In accordance with known technology for generating radio-frequency (RF) lesions, as described in the Cosman and Goldberg articles described above, a high-frequency signal applied to the exposed tip 2 generates a heated region around it, which in turn produces a heat lesion or ablation zone 37 around the exposed tip 2. The size of the ablation zone or heat lesion 37 is increased by increasing the power from the energy source 33 that is applied to the tissue. Thus, the size or volume of the ablation zone 37 can be graded and controlled around the urethral channel.

Also shown is a second cable 42 that is placed in conductive contact with a portion of the patient's skin S or other part of the body via a second electrode 44. The second electrode 44 serves, as is common practice, as a reference or return electrode for the RF current emitted from the RF electrode tip 2. Examples of RF lesion generators and RF electrodes using this configuration can be found in the product literature of Radionics, Inc., Burlington, Mass. The RF generator or energy source 33 may have temperature meters 48 or other lesion parameter readouts 51, illustrated by a digital meter reading, for display of power, current, voltage, impedance, or other parameters associated with the RF lesion process.

To give a specific illustration of how urinary blockage is reduced in accordance with the system of FIG. 1, an RF electrode 1 with a diameter of 2 mm is partially covered with an insulating coating 5 (the hatched area). A conductive portion of the electrode, namely a shaft, is fabricated from a conductive metal tube, such as stainless steel. For MRI compatibility, other materials with low magnetic susceptibility (such as high cobalt nickel content materials, e.g. Inconel or copper) may be used so that direct MRI imaging of the lesion process and electrode positioning can be done.

In the disclosed embodiment, the exposed electrode tip 2 has a length of approximately 5 to 20 mm. The tip has a hemispherical, rounded point on its distal end 7 to present abrasion or penetration of the urethra U. The electrode may be self-contained or sealed, as in Radionics type TM electrodes. Alternatively, it may be a flexible catheter-type electrode wherein the insulating coating 5 is a plastic, urethane, polyethylene, silicone, or other material. In this case, the electrode tip may be a conductive metal tip which is fused to the flexible catheter structure 5. Within the catheter may be electrical wires which connect to the exposed conductive tip 2 and are brought out to make connection with the external cable 30 through a hub 27.

In accordance with another embodiment of the invention, the electrode 1 may have an outer cannula, as in a needle, with an inner obdurating stylet to facilitate insertion. Once inserted into the urethra as in FIG. 1, the stylet may be removed and other structures inserted in its place, such as fiber optic endoscopic visualization probes, temperature sensing probes, multiple temperature-sensing probes, and so on. The electrode tip in any of these configurations may also include a temperature sensor built into the tip, or alternatively the system may include a temperature-monitoring probe that is inserted into the catheter or cannula once the instrument is in place within the urethra.

By carefully placing the RF electrode in accordance with FIG. 1 within the catheter and positioning the exposed conductive RF tip 2 in an appropriate portion of the urethra U where there is a urinary obstruction, an effective ablation of the prostate can be accomplished. By supplying an RF output from the energy source 33 to the tip 2, heating of the urethra adjacent to the tip 2 and the surrounding periurethral tissue in the vicinity of the tip will occur. In accordance with one embodiment, a heat lesion of desired size is formed by controlling the temperature of the heated urethra and prostate tissue immediately surrounding the RF electrode tip 2 to approximately 90° C. At this temperature, an ablation volume will be formed having a diameter of approximately 1 to 1.5 cm. This ablation volume will engulf the urethra and the periurethral tissue and be entirely contiguous with the remaining urethra connected to it. The size of the heat lesion is visualizable on CT or MRI image scanning at the same time or after the lesion is made.

In accordance with other embodiments, depending on the lesion sizes desired, other electrode tip temperatures or prostate tissue temperatures ranging between 50 and 100° C. are used. The desired lesion sizes are determined (for example 0.3 to 5.0 cm) depending on the size and geometry of the patient's prostate or urethral obstruction or other clinical considerations.

The energy source 33 has a power range from 0 to approximately 50 watts, although 20 watts or less is generally adequate to achieve the temperatures cited above. The electrode tip 2 has a temperature sensor built inside the electrode tip or on its surface, which may be a thermistor, thermocouple, or other type of temperature sensor. The temperature sensor is connected via connection wires extending inside the electrode shaft 1 to the energy source 33 including its meter 48, thereby enabling temperature monitoring by the clinician. The measured temperature at the electrode tip is representative of the temperature of the urethra and the nearby prostate tissue as the RF ablation proceeds.

The shaft of the electrode 1, in accordance with one embodiment of the invention, is approximately 20 to 30 cm in length. In other embodiments, lengths up to 60 cm may be used. It should be recognized that varying sizes, geometries, electrode tip configurations, tip diameters and lengths, etc. may be used for the RF electrode 1 to produce RF heat lesions.

The ultrasonic imaging device 11, which in one embodiment of the invention is the EPOXP Monitor available from Accuson company, Mountain View, Calif., is used to provide images on the display screen 24. The ultrasonic image on the display may show the electrode shaft 1 and the electrode tip as they are positioned within the prostate, and this is visualized on the screen display 24. The surface of the electrode tip 2 or the electrode shaft 1 is preferably roughened, scored, or otherwise configured to make it more visible via ultrasonic imaging.

The depth of penetration of the electrode 1 and its RF tip 2 within the prostate and urethra may be gauged by scale or indicating markings 40 on the shaft of the electrode 1 near its proximal end. If different positions of the electrode tip need to be implemented, the depth of insertion of the electrode in the penis and urethra can be changed according to the scale markings 40. For example, the ultrasonic image display 24 may indicate that the electrode tip 2 is too deep or too shallow within the urethral tract inside the prostate. Accordingly, the electrode shaft may be moved in or out quantitatively by the scale markings 40.

Figure 2:
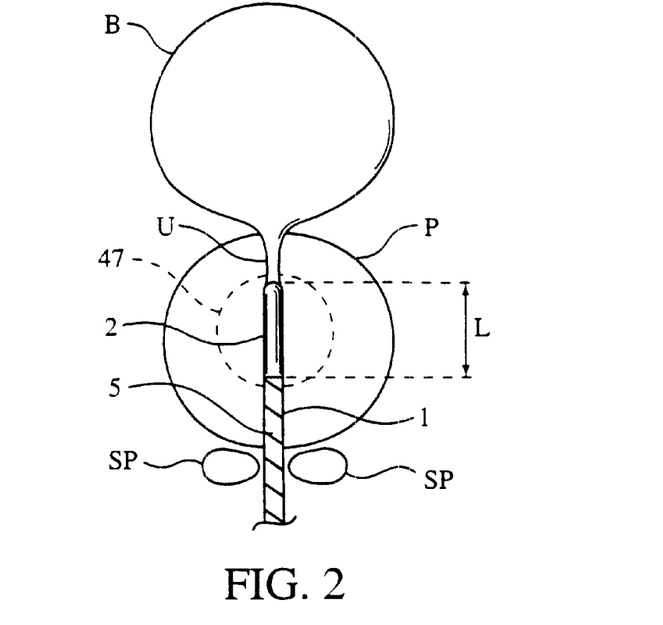
FIG. 2 illustrates a procedure or technique by which a radio-frequency electrode is located intraurethrally near a point of urethral obstruction in the prostate to make a radio-frequency (RF) lesion.

FIG. 2 shows a diagram illustrating the manner in which a thermal lesion is made by an RF electrode placed intraurethrally. Generally, a patient's bladder B is illustrated; it is in fluid communication with the patient's urethra U. The RF electrode 1 is inserted into the urethra U, as shown, to place the RF electrode tip 2 within the urethra near a point of urethral obstruction. As above, the shaft of the electrode 1 is has an insulated portion 5 (the hatched area). When RF energy is delivered from the energy source 33, as in FIG. 1, dissipation of the energy around the RF electrode tip 2 causes a heating zone to occur around the tip. This will cause a zone of heat ablation 47, which engulfs the urethra U and the periurethral tissue within the dashed line volume. The zone 47 indicated by the dashed line would, for example, illustrate a typical isotherm surface area or area of constant temperature within which all tissue is raised to a lethal or ablation temperature. An example of a desired temperature for ablation to kill prostate tissue is approximately 50° C. maintained for six minutes. It should be recognized that variations, depending on the desired outcome, are possible.

An ablation isotherm surface, therefore, is an indication of the region in which the cells are dead. At 50° C. or higher temperatures, tissue necrosis in the isotherms within the volume encompassed by the isotherm surface area is induced. Liquefaction of the necrotic tissue occurs within days from the day of treatment. If such an ablation isotherm area (corresponding to ablation or necrosis), as illustrated by the dashed line 47, engulfs the urethra in the region where there is a urethral restriction, then in a matter of days after treatment, the entire periurethral zone, including the urethra within the isotherm surface area, is obliterated and liquefied. The flow of urine from the bladder through the urethra will then carry away the liquefaction and debris from the necrotic tissue away and out of the body through the urethra.

Figure 3:
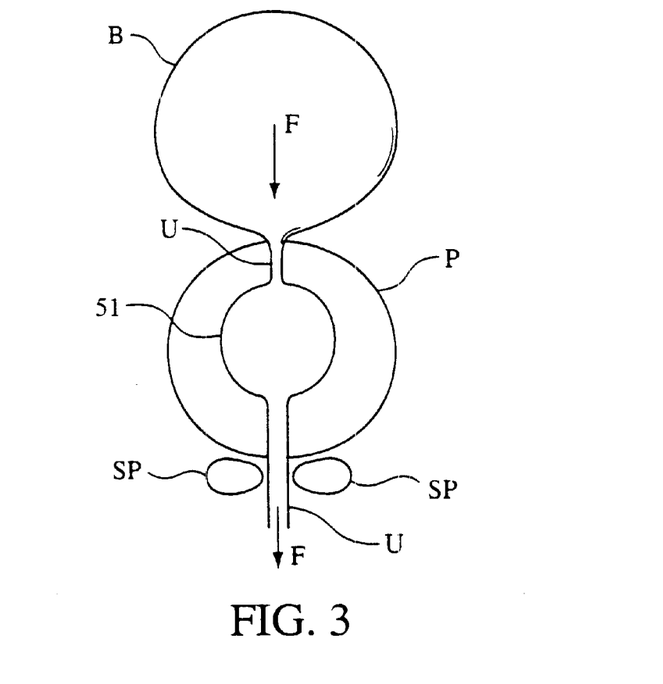
FIG. 3 illustrates a cavity in the prostate contiguous with the urethra induced by a system and method according to the present invention.

FIG. 3 illustrates the effects induced by the system and method for RF urethral enlargement by thermal ablation according to the present invention. The inventive system and procedure obliterates the urethra and region within the ablation isotherm surface boundary to induce a cavity 51. The urethra and prostatic tissue that previously was within this cavity volume has been necrosed and liquefied and passed out through the urethra U by the flow of urine, indicated by the arrows F, from the bladder B out through the penis PN (FIG. 1). The urethral wall has been obliterated to open the channel in communication with the remaining segments of the urethra. The cavity 51 is generally symmetric about the urethra to open a lumenal volume, thereby reducing the restriction of flow that previously existed with the urethral obstruction. Because the cavity 51 is located around the urethra, it is typically axially central to the prostatic gland. There is the advantage that the cavity has a smooth, contiguous continuity with the urethral structures connected to it, increasing the likelihood of laminar fluid flow after the cavity 51 has been formed. Since it is in the periurethral region, the inventive technique also has the advantage that it is remote from various critical structures such as nerves in the outer prostate and the rectal wall.

By way of further explanation, the urethral wall and the periurethral tissue that is in the area of the zone of necrosis is liquefied and carried away by urine flow F. As the urethral cross-sectional area is increased, the impedance to flow of the urine is substantially reduced and the flow vector F is increased in magnitude, restoring normal voiding function or improving voiding rate. The body reacts to this procedure by creating a new epithelial layer of cells, within a matter of a few weeks, to cover the interior surface of the cavity 51.

Because a typical isotherm surface area 47 (FIG. 2) is created in a generally central area of the prostate because of the intraurethral location of the RF electrode, the peripheral annulus of the prostate acts as a natural margin of safety or thermal buffer zone for the critical organs, which typically lie outside the peripheral region or just outside the prostate. These would include critical nervous structures and the rectum wall and mucosa.

During the process of carefully positioning the RF electrode tip 2 relative to the urethral obstruction and the prostate (as illustrated in FIG. 2), a visualization representation is relayed via the ultrasonic detector or imaging head 14 and displayed on the ultrasonic display 24 (FIG. 1). This allows the RF electrode tip 2 to be safely guided and located in the proper region of the prostate and away from delicate regions such as the sphincter SP.

The length L of the exposed RF electrode tip 2 may vary or be chosen according to the length of the length of the ablative isotherm volume 47 required. For a fixed length L, the position of the electrode tip 2 may be translated after a first lesion to another position within the prostate to enlarge the length of the cavity 51 (FIG. 3). Thus, multiple RF ablation stages may be considered according to clinical needs to enlarge the length of the urethral cavity enhancement.

In accordance with another embodiment of the present invention, the RF electrode may not include the temperature sensor. The correlation of an ablation size desired to a certain electrode tip geometry may be determined by considering RF generator parameters such as power output, voltage, and current. Generally, it can be determined that ablation temperatures of greater than 50° C. in the prostate tissue can be induced, for example, by way of RF power or current levels greater than known amounts. This information can be used by clinicians to induce sufficient ablation sizes to alleviate urinary obstructions by the intraurethral method, depending on clinical circumstances.

In the disclosed embodiment of the invention, the RF electrode itself is self-contained, having a unitized metal shaft such as a tube of stainless steel or other material with an enclosed, sealed tip. Inside the electrode tip 2 is a thermocouple, thermistor, or other temperature sensor. The sensor may be in the interior of the tip or integral with the surface of the tip. The electrode shaft may be electrically insulated by any of various suitable materials, sheaths, or coating, such as epoxy, Teflon, etc. The hub 27 of the electrode 1 (FIG. 1) may be tubular or otherwise shaped to best conform to the operator's fingers as he inserts it intraurethrally.

As described previously, the shaft of the electrode 1 or the RF tip 2 may have properties to optimize visualization. For example, a roughened surface on the tip 2 can make it more exogenic and visible in ultrasonic imaging. Furthermore, a metal tip may be visible in an X-ray image to locate the position of the tip in the prostate during the procedure. Alternatively, the electrode may be made of MRI or CT compatible material so that it is visible in MRI or CT imaging without substantial artifacts. These imaging techniques may be used prior, during, or after the procedure to monitor the placement of the electrode and the progress of the necrotic periurethral cavity after ablation.

In accordance with another embodiment of the invention, the RF electrode 1 as shown in FIG. 1 has an insulated shaft made of a flexible material such as plastic, silicone, polyurethane, etc. It may be similar to a catheter with a hollow interior to enclose the electrical connection or temperature sensing wires. The RF tip is made of metal and is bonded or connected to the flexible insulated shaft portion 5 by bonding agents, glue, swaging, or other means. A flexible catheter-like electrode has the advantage of being placed into the urethra U with greater ease and comfort to the patient.

Figure 4:
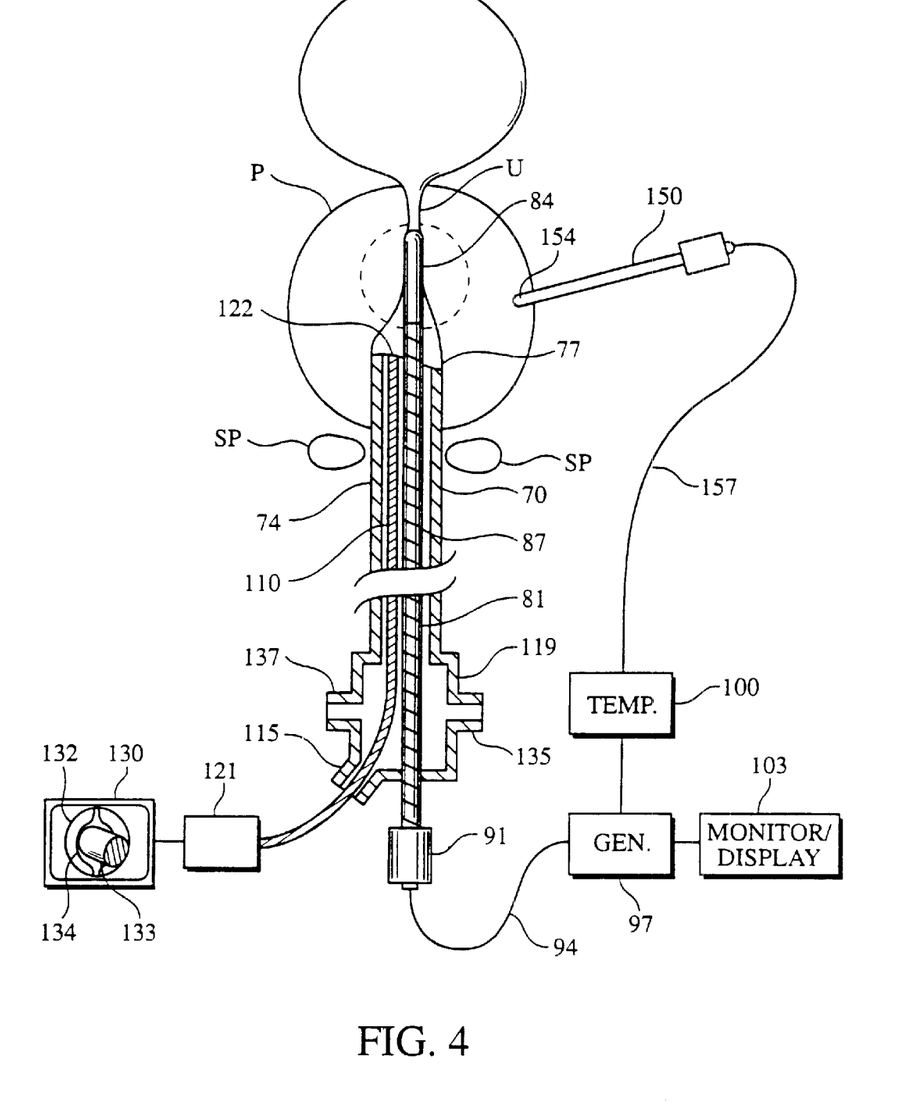
FIG. 4 shows another embodiment of a prostate ablation electrode in combination with an endoscope passed into the urethra in accordance with the present invention.

FIG. 4 illustrates another embodiment in accordance with the present invention. An endoscope 70 is illustrated in sectional view, and has a cannula 74 which is inserted into the urethra, which is common practice for urologists. The endoscope 70 has a tip end 77 that is inserted past the sphincter and into the prostate region P. A radio-frequency electrode 81 is then inserted through the endoscope cannula 74. It has an exposed, conductive RF tip 84 that extends beyond the endoscope tip 77 and remains within the urethra U. As in the previously described embodiment, the shaft of the electrode 81 has an insulated surface portion 87 (hatched lines). The RF electrode 81 further has a hub 91, facilitating connection via a connecting cable 94 to a generator 97, serving as a source of high frequency output. A temperature-sensing readout 100 is used to read the temperature of the temperature sensor which is located within the RF electrode tip 84 or by multiple temperature sensors located at other points along the electrode shaft 81. Readout of RF output parameters from the generator 97 can be accomplished by a monitor and display system 103, which in various embodiments may involve computers, controls, feedback systems, electronics, and even computer graphic displays to illustrate the parameters by a computer graphic workstation during the progress of the ablation.

Also shown in FIG. 4 is an optical visualization system which can be used in conjunction with the endoscope 70 and RF electrode 81 in accordance with the present invention. An optical visualization element 110 is shown passed through the cannula 74. In the disclosed embodiment, this element 110 is a fiber optic channel inserted through a port 115 on a hub 119 of the endoscope 70. A fiber optic control unit 121 processes the signal from the fiber optic channel 110, and also may control illumination sources that can provide illumination down the fiber optic channel into the region of the prostate near the RF electrode tip 84. A processing display unit 130 can display an image field 132 as seen by the fiber optic channel 110 near the RF electrode tip 84. The display is capable of showing an image 133 of the RF electrode 81 with respect to an image 134 of the urethra. Accordingly, at the tip 122 of the fiber optic line channel, a view of the region in the prostate where the RF ablation will take place can be displayed on the display 130. The position of the RF electrode tip 84 within the urethra U can be visualized prior, during, and after RF heating. In this way, control of the position of the RF electrode within the urethra can be accomplished under direct visualization, increasing the safety and certainty of the intraurethral technique.

By way of explanation, the use of cystoscopes or endoscopes in the urethra is common practice by urologists. A common cystoscope in use is the Urethroscope made by the Karl Storz comkpany of Tuttlingen, Germany. Such devices commonly have fiber optic channels and imaging systems such as those illustrated in the description of FIG. 4, above. They also may have optional irrigation ports 135 and aspiration ports 137, also illustrated in FIG. 4. Because the RF electrode tip 84 of the present system and method, as illustrated in FIG. 4, is under direct visual control by the endoscope fiber optic apparatus and display 130, better control and certainty of the placement of the electrode tip within the urethra and prostate is known. This is an advantage over the TUNA procedure, in which side-outlet radiofrequency electrode probes puncture the urethra and are therefore out of view of endoscopic fiber optic visualization.

Also referring to FIG. 4 and in accordance with the present invention, other temperature sensors may be placed in the prostate or nearby organs to monitor the process of the intraurethral RF electrode ablation. For example, a temperature-sensing probe 150 may be placed within the prostate, for example, through the rectal wall. It has a temperature-sensing tip 154 which measures the temperature in the peripheral region of the prostate P. A connection cable 157 reads out the temperature from the temperature sensor 154 and passes a signal representative of the temperature to the temperature-sensing readout 100 in connection with the high-frequency generator 97 and the control apparatus 103. Multiple satellite temperature-monitoring sensors may accordingly be present to qualify the thermal distribution, particularly in regions of organs at risk.

Figure 5:
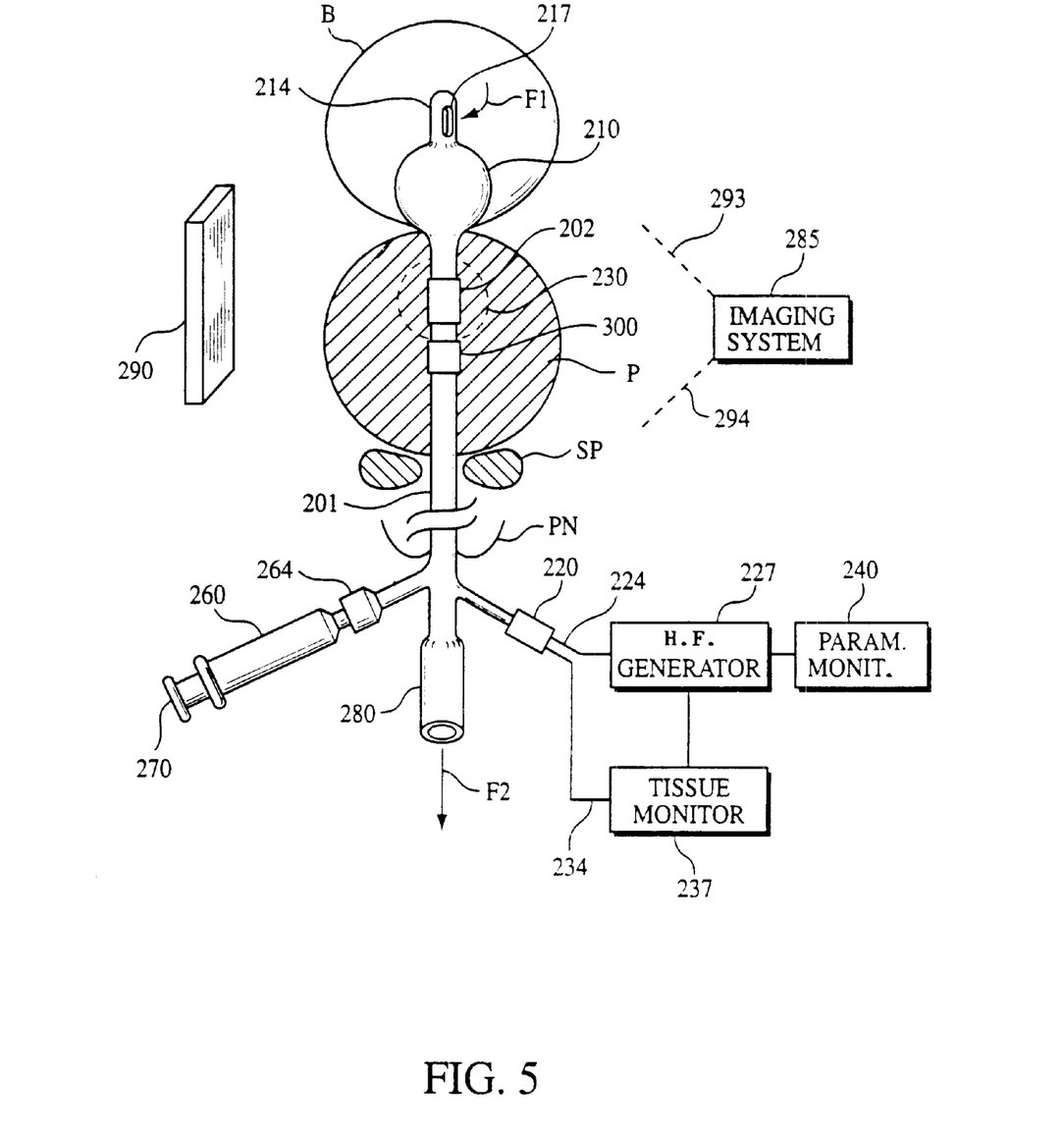
FIG. 5 shows another embodiment of a prostate ablation electrode integrated with a balloon catheter with multiple temperature sensors in accordance with the present invention.

FIG. 5 shows yet another embodiment of the system and procedure according to the present invention involving a catheter 201, which is passed into the urethra through the penis PN, which is shown only in partial sectional view. The catheter 201 has an RF electrode ring structure 202, which is positioned in prostate P according to clinical needs to alleviate urethral obstruction. At the distal end of the catheter, there is an inflatable balloon structure 210 shown in an inflated state. There is further a distal tip 214 which defines an opening 217. Urine within bladder B can flow according to an arrow F1 into the opening 217 and out of a proximal end of the catheter, as illustrated by an arrow F2.

Rubber catheters with balloon ends are used commonly by urologists. Examples of such catheters are SILASTIC Foley catheters distributed by the Bard Urological Division of Covington, Ga. FIG. 5 shows an embodiment of the present invention in which such a catheter is augmented by the RF ring structure 202. In the disclosed embodiment, the ring structure 202 is connected internally through the catheter 201 to an RF hub portion 220, a connection cable 224, and a high-frequency generator 227. The generator 227 supplies a high frequency such as RF output, as described in connection with the previous examples, to the RF electrode ring structure 202. The resulting heating by high frequency current can give rise to an ablation isotherm surface 203 (the dashed line). Temperature sensors may be located at multiple points along the catheter 201 within the prostate, and temperature signals carried by a connection 234 to a tissue temperature monitor 237 to monitor the ablation process as described previously. Additionally, monitoring of high frequency output parameters from the generator 227 may be accomplished via a parameter monitor 240.

The system in accordance with the present invention, illustrated in FIG. 5, may be implemented by the following illustrated example. The catheter 201 is sterile and disposable; it includes an RF ring structure 202 with hub or connection structures 220, as described above. The catheter 201 is inserted into the penis PN according to common practice until the balloon structure 210 is within the bladder B. The balloon is then inflated by a syringe 260 attached to an inflation hub 264, which is standard on Foley balloon catheters. Inflation by the syringe plunger 270 injects air or fluid into the balloon 210, thereby inflating the balloon and retaining it within the bladder B. If fluid is injected to fill the balloon, be contrast fluid that is visible on X-ray or fluoroscopic images of the patient's body can be used to confirm the balloon's position.

Once the balloon catheter is so entrapped within the bladder B by the inflation of the balloon 210, urine within the bladder B can flow according to the arrow F1 through the distal tip opening 217, and drain from a main catheter hub 280, as illustrated by the arrow F2. Once this configuration is established, an X-ray contrast medium may be injected through the hub 280 into the bladder B. An imaging system 285 such as a fluoroscope or X-ray machine can then be used to image the catheter tip 214, the balloon 210, the bladder B, and the RF electrode ring structure 202 together. An X-ray imaging detector 290 is shown which can collect X-ray images from X-rays emitted from an imaging system 285, as illustrated, within the field of imaging illustrated by dashed lines 293 and 294. Such X-ray images visualize and assure that the RF electrode ring structure 202 is properly placed with respect to the bladder B and the prostate P. It will increase the safety that the RF ring structure 202 is within the prostate at the point of urethral obstruction and sufficiently away from the apex of the prostate or the sphincter SP, which are critical structures.

The embodiment of FIG. 5 shows the RF electrode ring structure 202 in an intraurethral position. As with the previously described embodiments, the heat ablation associated with the ring structure 202 will obliterate and necrose the urethra and periurethral prostatic tissue proximate to the RF electrode ring 202. Also shown on the catheter 201 is a second element 300 which in various embodiments can be a second RF electrode or a temperature sensor. For example, if the region of ablation 230 (the dashed line) needs to extended to include a region around the electrode 300, then the output from the generator 227 could be applied to the electrode 300. This illustrates that multiple RF electrodes can be placed on the same catheter structure 201 to grade the size of the ablation according to clinical needs.

Alternatively, if the structure 300 contains temperature sensors, then the tissue monitor 237 can read out tissue temperature near the structure 300 as an indication of ablation size. For example, if the temperature sensor in 300 reads less than 50° C., then this would indicate that the ablation zone 230 has not reached into the region near the structure 300.

In the exemplary embodiment of FIG. 5, the catheter 201 is made from SILASTIC rubber, as manufactured by Dow Corning, of Minneapolis, Minn. Its diameter is approximately 3 to 8 mm, and its length is in the range of 30 to 40 cm. However, other smaller or larger dimensions may suit varying clinical needs. The electrode structures 202 and 300 are made from stainless steel rings and bonded to the SILASTIC substrate of the catheter 201. Other materials or platings may also be used, including but not limited to Inconel, titanium, or copper plated with gold, to suit various clinical needs. The balloon structure and body of the catheter could be similar to the Foley catheter mentioned above with inflatable balloon 210, distal tip 214, port 217, an injection port 264, and the main catheter urinary hub 280. In addition, the hub or other connection 220 for the high frequency and thermal monitoring cabling can be adapted. Internal connection wires within the SILASTIC rubber body of the catheter 201 connect to the RF electrodes 202 and 300, as well as temperature sensors within the catheter at various points.

A urological RF catheter, as in FIG. 5, is easily inserted into the urethra and can remain in place within the patient for several days. Diagnostic X-ray images can be taken with an X-ray imaging machine, as illustrated by the X-ray system 285 and the imaging detector 290. This confirms the position of the RF electrode ring 202 in the prostate. Intraurethral RF ablation is performed when the positioning of the catheter is appropriate, and can be repeated and enlarged as necessary according to the description above. As stated above, the catheter can be left in place in the patient with the balloon inflated for several days after ablation until the ablated zone has fully liquefied. The catheter balloon can then be deflated, and the catheter removed from the urethra, whereupon the necrotic fluid from the ablation zone and the obliterated portion of urethral tissue will be washed away by the urine flow from the bladder B out the urethral channel.

One advantage or using a catheter-type RF electrode such as the embodiment shown in FIG. 5 is that minimal anesthesia is necessary in inserting the electrode into the urethra.

Such catheter structures are familiar to urologists and can be inserted into the patient in the supine position with ease and comfort. A further advantage is that no endoscope is needed to insert it into the urethra or to visualize its position in the prostate. It can be used in an office setting, and not necessarily in a sterile operating room environment, thereby making the procedure more widely available to patients by reducing reduces hospital expenses. It is also relatively economical because it has low construction complexity and can thus be used disposably from a factory-packaged sterile pouch.

Figure 6:
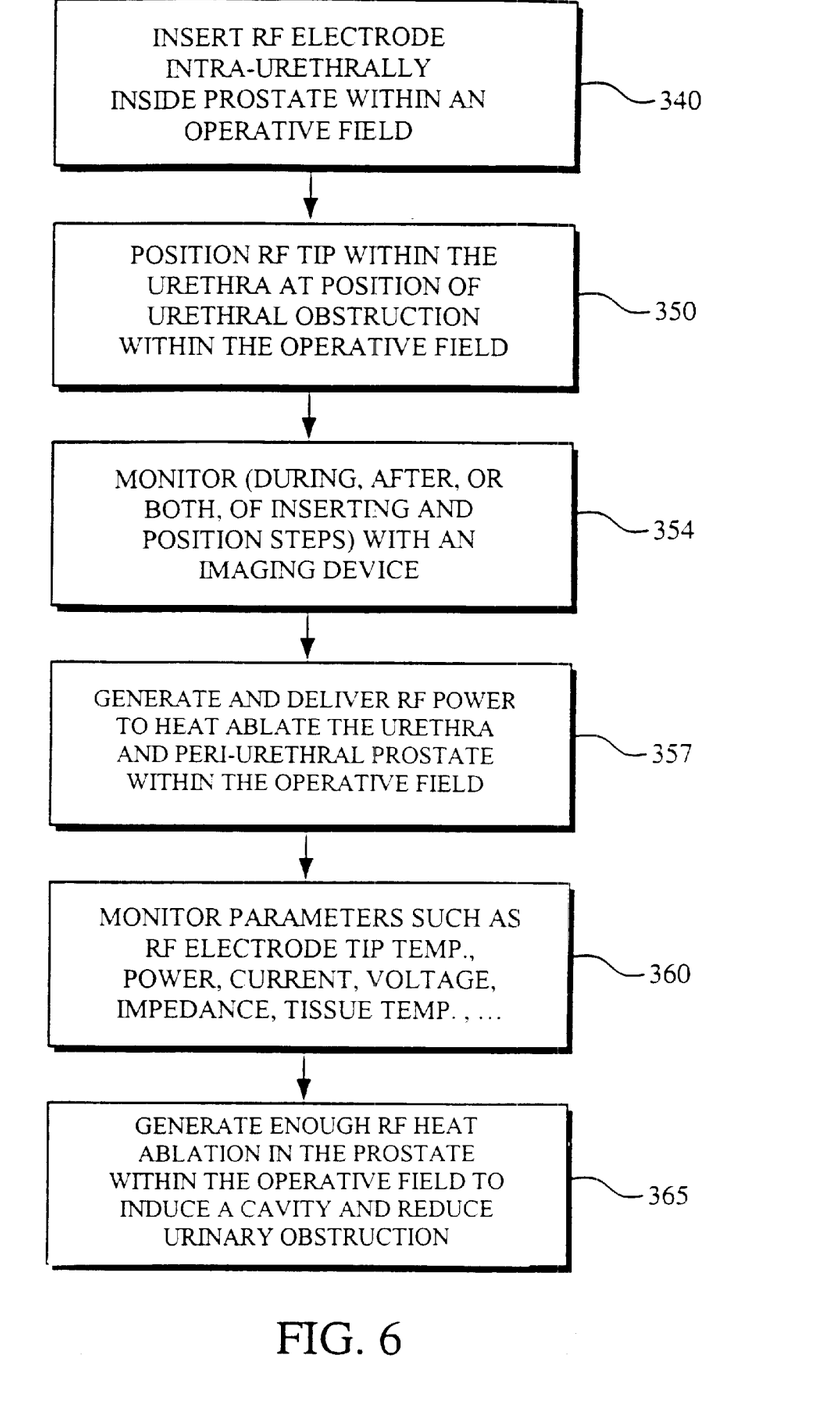
FIG. 6 shows a flow chart of the process employed in operating a system in accordance with the present invention.

Referring now to FIG. 6, a flow chart is shown to illustrate the process of intraurethral RF ablation for relief of urinary obstruction. The procedure starts by inserting the RF electrode, such as any one of those described above, intraurethrally into the prostate (step 340), as illustrated in FIG. 1, for example. The positioning of the RF electrode tip (e.g., the tip 2 of FIG. 1 or the RF ring 202 of FIG. 5) within the urethra at the appropriate position of urethral obstruction is then performed (step 350). This step may involve the use of ultrasonic, CT, MR, or X-ray imaging measuring the electrode's depth in the urethra, the use of endoscopic visualization, or other positioning techniques. In the case of a balloon catheter, contrast injection into the balloon or the bladder followed by X-ray imaging is another way of positioning the RF tip in the appropriate position. The position of the electrode in the urethra relative to the prostate is monitored (step 354). The use of CT, N, ultrasound, X-rays, fluoroscopes, or other imaging devices may be used during this step, as they also may be used in the positioning step (step 350).

When the RF electrode tip is in the proper position within the prostate, the step of generating and delivering high frequency power to heat ablate the urethra and periurethral prostate within the operative field is performed (step 357). This can involve elevating the voltage, current, or power applied by the high frequency generator. The generator may have manual controls such as knobs or other elements to control its output levels that can be actuated at this point. Alternatively, the process may be automated with a set power or temperature level predetermined on the generator control system and an automatic or semi-automatic achievement of that high frequency control parameter reached by an appropriate feedback and control system within the generator. These elements could all be built into the energy source 33, for example, illustrated in FIG. 1.

The actual parameters of the RF power delivered to the RF electrode within the urethra may be recorded and monitored (step 360). Parameters of interest can include the temperature recorded at the RF electrode tip, the temperatures recorded at satellite electrodes placed in the prostate or in the neighboring operative field, the RF power, current, voltage, impedance, and so on. The time of RF power application may also be monitored at this step and a predetermined set time of exposure of the RF power to the electrode may be desirable, depending on clinical needs, or may depend on the reading of temperature sensors in the prostate or the RF electrode at various positions. Knowledge of these RF parameters and the geometry and size of the electrode and RF electrode tip assist in guiding the surgeon as to the size of the lesion and resultant urethral/prostatic cavity that is produced. For example, it may be known from clinical experience that certain size ablations can be induced for certain electrode geometry types with a known value of RF power, current, or voltage, or alternatively a known temperature as recorded in one or more of the temperature monitors. As represented in FIG. 6, these parameters may be monitored during the ablation process and influence the decision of the clinician to terminate or continue the process according to experience and parameter values. Measurement of such parameters is accomplished by lesion generator systems of Radionics (Burlington, Mass.).

The adequacy of the duration and parameter sets to achieve the correct RF heat ablation in the prostate and to reduce urinary obstruction is determined (step 365). The decision to stop the procedure when it is believed that the cavity is adequate can be made in this step.

In accordance with one embodiment of the present invention, the clinician may choose an RF electrode tip geometry of a certain size, diameter, and length. He may know from experience that the insertion of such an electrode intraurethrally with the electrode having a temperature sensor and delivering RF power to raise the tissue temperature so that the electrode tip is elevated to a certain temperature level will produce a known and generally adequate ablation cavity. This set of criteria may be used by the clinician to induce sufficient ablation sizes to alleviate urinary obstruction according to the clinical circumstances.

In accordance with another embodiment of the present invention, the RF electrode may not include a temperature sensor. The correlation of ablation size desired for a given electrode tip geometry may be determined by considering RF parameters such as power, output, voltage, and current. Generally, it can be determined that ablation temperatures of greater than 50° C. in the prostate tissue can be induced, for example, by RF power or RF current levels greater than known amounts. In that embodiment, these RF power and current parameters may be used by the clinician for a given time of ablation exposure to alleviate the urinary obstruction by creating a sufficient intraurethral cavity. It is understood that a range of these parameters and time exposures, as well as various electrode geometries, may be used to grade the size of the ablation cavity according to the experience acquired by clinicians with this technique.

In accordance with one embodiment of the present invention, if CT, MR, or other imaging techniques are used during ablation, then they may be used to decide on adequate ablation size. For example, certain MR images can represent thermal distribution around the electrode, and thus indicate the ablation zone.

Figure 7:
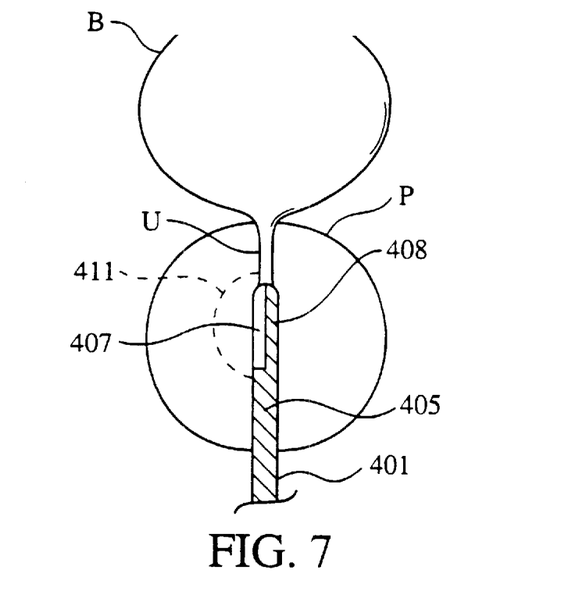
FIG. 7 shows another embodiment of a prostate ablation electrode according to the invention having an asymmetric conductive tip.

FIG. 7 illustrates another embodiment of the invention, in which the prostate P, the bladder B, and the urethra U are shown in partial sectional view. An RF electrode 401 is inserted into the urethra U. As in various other disclosed embodiments, the electrode 401 has an insulated portion 405 (shown as hatched lines). However, an exposed conductive RF tip 407 in this embodiment is asymmetrically configured at the end of the elongated RF electrode 401. The distal tip of the RF electrode has an insulated side portion 408 to prevent that portion of the patient's urethra R from being exposed to current from the RF generator (not shown in FIG. 7, but illustrated in FIGS. 1, 4, and 5). The heating zone in this embodiment tends to lie proximate to the exposed RF tip portion 407. To illustrate the ablation zone, a dashed line 411 is distributed laterally on a side of the urethra U corresponding to the exposed side portion 407 of the RF electrode tip. The exposed side portion 407 may take various shapes to suit various clinical uses, such as partial cylindrical surfaces, discrete areas of conductive exposure, lines or wires of exposed conductors on the electrode 401, and so on. This embodiment can be particularly advantageous when ablation should be directed asymmetrically to a particular portion of the patient's prostate.

Figure 8:
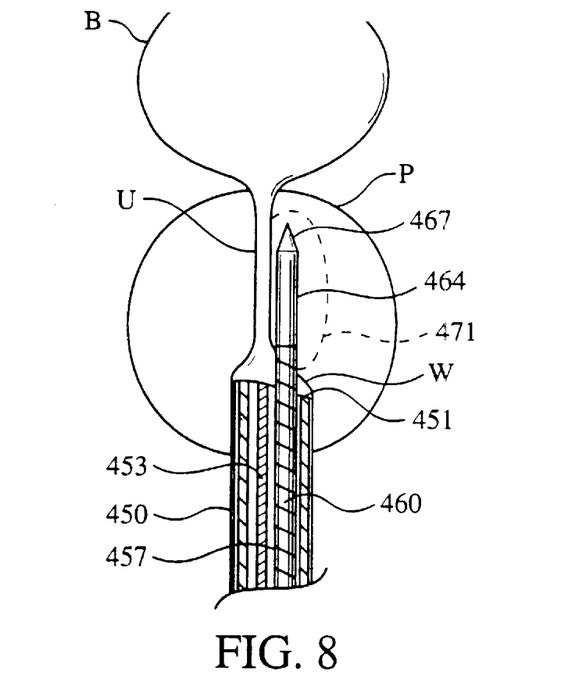
FIG. 8 illustrates another embodiment of prostate ablation electrode according to the invention having a pointed conductive tip, which is adapted to be used in conjunction with a cystoscope.

FIG. 8 illustrates another embodiment of the invention, in which a cystoscope 450 is placed in the patients urethra U. An RF electrode 457 is passed through the cystoscope shaft 450; it has an insulated portion 460 (shaded area). An RF tip 464 emerges from a distal end 451 of the cystoscope 450. The RF tip 464 defines a relatively sharp point 467, which is capable of piercing the urethra wall W. The RF tip 464 emerges approximately frontally from the cystoscope end 451, and it can be visualized by an optical channel 453 as it pierces the wall W. In this embodiment, connecting the RF tip 464 to the RF generator (not shown) will ablatively heat the prostate tissue near the RF tip 464. An ablation volume 471 (illustrated by a dashed line) around the RF tip 464 and can thereby be placed asymmetrically on one side of the urethra U to suit various clinical needs.

The use of intraurethral RF electrodes herein has the advantages of simplicity, economy, control, consistency, reproducibility, and patient tolerance compared to other techniques aimed at treating BPH or prostate cancer such as TURP, TUNA, and other methods described above. The present system and method maintains the RF electrode tip within the urethra, and does not pierce the urethral wall. As described, the heat ablation process using an intraurethral electrode according to the invention has the effect of ablating the urethral wall and periurethral tissue to open the channel and to destroy the urethra near the electrode. This has advantages over other methods and apparatus which seek to leave the urethra intact or unablated, such as TUNA or McGahan et al.'s procedure cited above. In the present invention, because the electrode does not pierce the urethra, the risk of hemorrhage is reduced. Furthermore, with the RF electrode tip within the urethra and under direct endoscopic visualization or other imaging control, there is a more exact knowledge of the ablation zone in the central prostate region to reduce the chance of damaging sensitive structures. Thus, with patients in whom bleeding is a problem, such as those in frail health or on anti-coagulation medication for cardiac or neurological disorders, the present intraurethral approach has an advantage over approaches such as TURP and TUNA where deliberate scraping, cutting, or piercing of the urethra will cause irritation and bleeding.

A further advantage of the present invention is that there is more precise control of the placement of the electrode tip in the prostate. In its various embodiments, it is visualizable within the urethra using an endoscope or cystoscope, measurable in insertion depth into the urethra, and visualizable with ultrasound, X-rays, CT, or MRI. Therefore, the positioning and extent of the ablation zone is better controlled with the present invention than other techniques. Furthermore, because the present technique locates the ablative cavity in the central periurethral area by its electrode placement, the risk of damage to the rectal mucosa, the rectal wall, neural structures, or seminal channels is reduced.

A further advantage of the present system and method is that it is directed at widening the urethral channel without preserving the urethra itself. This is in contrast to the TUNA procedure or the technique of McGahan in which preservation of the urethra itself is an objective. In the present invention, an objective is destruction of the urethra near the site of the RF electrode's tip. This has the advantage that the region of necrosis, including the urethra and surrounding prostatic tissue, will be liquefied and swept away by the urine passing through the urethra without the possibility of entrapment of coagulated tissue or necrotic material outside of the urethra. Such entrapment is possible in the case of TUNA or McGahan et al.'s procedure, where regions of ablation and necrosis are outside the intact urethra. This can cause swelling of the tissue around the urethra as absorption of necrotic tissue proceeds, resulting in continued pressure to the urethra and further closing down of the urethral channel. There is also the disadvantage that an increase in osmotic particles within the interstitial prostatic medium can take days or weeks to absorb, resulting in extended irritation, obstruction, and risk. In the present invention, this post-ablation debris is naturally swept away from the urethral cavity and contiguous urethral stream, thus avoiding the above-mentioned disadvantages of other techniques.

Because it is better-tolerated and of less risky and expense than TURP, TUNA, and non-central radio-frequency lesion making (viz. McGahan, et al.), the present invention is indicated for a wider population of patients, and potentially will achieve more effective clinical results. And because the present technique widens the urethral channel, as does, for example, TURP, but without the side effects of bleeding and with the need for only minimal anesthetic and no hospitalization, the present invention will be far better tolerated by patients, especially those who are in frail health for whom a TURP procedure may be too risky to endure.

The present system and method of intraurethral ablation has the further advantage of safety compared to TURP, TUNA, or non-central lesion approaches (such as McGahan, et al.) Urologists are trained to do catheter or cystoscopic placements in the urethra, as for the present system and method, and thus the electrode placement is natural and safe to be performed. The electrode placement being visualizable in the present invention has the advantage of control compared to TURP, TUNA, or non-central RF lesions where exact position or degree of resection is less definite and non-visualizable in some cases. Minimal anesthetic is required for the present invention, which is not the case for TURP, where bleeding and discomfort is significant. Minimizing anesthetic is important for patient comfort, as well as in cases of patient fragility. The use of a flexible catheter or a non-flexible electrode within an endoscope is easily tolerated by the patient and enables an exact positioning of the RF electrode tip within the prostatic body, yielding safer knowledge of the ablative cavity position.

Yet another advantage of the present invention is that the ablation cavity is made contiguous to and central to the stream of the urethral passage. Thus, the urethral enlargement is a smooth, symmetrically placed cavity. This will produce a more laminar flow of the urine from the bladder through the urethra, which in turn will reduce the turbulence and possibility pockets of stagnation of fluid in the resulting widening of the prostatic passage.

Yet a further advantage of the present procedure is that the electrode system is simple compared to the instrumentation of TURP and TUNA. This will lead to a less expensive procedure than TURP or TUNA procedures, making it amenable and more cost effective for a wider patient population. The use of a flexible balloon RF catheter, as one embodiment cited above, has the advantage of economy and simplicity of structure as well as providing a disposable device that ensures sterility and cleanliness for each application.

Forms and embodiments of the intraurethral radio-frequency urethral ablation system and method are provided involving various electrode designs with and without temperature monitoring, and in various electrode geometries. However, it should be recognized that other obvious forms may be used. For example, various materials, configurations, and control and display systems can be employed in a system or method for performing intraurethral prostate ablation without departing from the scope of the invention.

In view of these considerations, as would be apparent by persons skilled in the art, implementations and system should be considered broadly and with reference to the claims set forth below.

What is claimed is:

1. A method of alleviating urethral obstruction in a patient comprising:
   inserting a distal portion of an elongate member into the urethra of the patient without piercing the wall of the urethra, the elongate member having a conductive element disposed on an outer surface of the distal portion of the elongate member; and
   applying a high-frequency output through the conductive element for six minutes or less.

2. The method of claim 1, further comprising monitoring the position of a portion of the elongate member in the urethra using an ultrasonic image scanner.

3. The method of claim 1, further comprising generating image representations of a portion of the elongate member for guiding the elongate member in the urethra via CT or MR imaging scanner.

4. The method of claim 1, further comprising detecting a temperature level of the tissue proximate to the conductive element with a temperature sensor in the elongate member coupled to an external temperature monitor, the temperature being at least 50° C.

5. The method of claim 1, further comprising:
   inflating a balloon tip of the elongate member inside the bladder of the patient.

6. The method of claim 1, further comprising generating image representations of a portion of the elongate member in the urethra with an X-ray imaging apparatus.

7. The method of claim 1, wherein applying the high-frequency output includes forming a cavity such that the urethral passage is enlarged relative to a normal size of the urethral passage.

8. The method of claim 1, wherein the conductive element includes a ring electrode.

9. A method of altering tissue to relieve the symptoms of benign prostatic hyperplasia in a patient comprising:
   inserting a distal portion of an elongate member into the urethra through the penis to a region of the prostate without piercing the wall of the urethra, the elongate member having an active ring electrode disposed on an outer surface of the distal portion;
   connecting the electrode to a high-frequency generator; and
   applying a high-frequency output through the electrode to elevate the temperature of a portion of the urethra in the region of the prostate to at least 50° C.

10. The method of claim 9, further comprising generating an image representation of the position of a portion of the elongate member in the region of the prostate by utilizing an imaging apparatus.

11. The method of claim 10, where in generating the image comprises inserting an ultrasonic image scanner into the rectum of the patient to visualize the prostate and the position of a portion of the elongate member within the region of the prostate.

12. The method of claim 10, wherein generating the image comprises scanning the patient with a CT or MR image scanner to visualize the prostate and the position of a portion of the elongate member within the region of the prostate.

13. The method of claim 10, wherein generating the image comprises taking X-ray images to visualize the prostate and the position of a portion of the elongate member within the region of the prostate.

14. The method of claim 9, further comprising inflating a balloon tip of the elongate member so that the elongate member is stably positioned in the urethra.

15. The method of claim 9, wherein applying the output includes enlarging the urethra relative to a normal size of the urethra.

16. The method of claim 9, wherein applying the output includes applying the output through the ring electrode to a return electrode.

17. The method of claim 9, wherein applying the output includes ablating urethral or prostate tissue.

18. A method of altering tissue to relieve the symptoms of benign prostatic hyperplasia in a patient comprising:

placing a distal portion of an elongate member intraurethrally into the urethral passage, the elongate member having a conductive element, and energizing the conductive element in the urethral passage with high frequency energy for six minutes or less.

19. The method of claim 18, wherein energizing the conductive element alleviates urethral obstruction.

20. The method of claim 19, wherein alleviating urethral obstruction includes forming a cavity in the urethral passage and adjacent prostate tissue having a diameter in the range of about 0.3 to 5 cm.

21. The method of claim 18, wherein energizing the conductive element includes connecting the conductive element to a high frequency generator.

22. The method of claim 18, wherein energizing the conductive element includes forming the cavity such that the urethral passage is enlarged relative to a normal of the urethral passage.

23. The method of claim 18, wherein energizing the conductive element includes applying the high frequency energy through the conductive element to a return electrode.

24. The method of claim 18, further comprising imaging a portion of the elongate member to monitor the position of the elongate member.

25. The method of claim 24, wherein imaging includes ultrasonic imaging.

26. The method of claim 25, wherein imaging includes inserting an ultrasonic scanner transrectally.

27. The method of claim 24, wherein imaging includes CT imaging.

28. The method of claim 24, wherein imaging includes MR imaging.

29. The method of claim 28, further comprising detecting a temperature level of tissue surrounding the conductive element.

30. The method of claim 28, wherein energizing the conductive element causes emission of current from the conductive element and dissipation of energy into tissue around the conductive element.

31. A method of treating the symptoms of urinary obstruction in a patient comprising:

inserting a distal portion of an elongate member into a urethral passage to a region of the prostate of the patient, the elongate member having a ring electrode disposed on an outer surface of the distal portion, and energizing the ring electrode with high frequency energy to elevate the temperature of a portion of the urethra in the region of the prostate to at least 50° C.

32. The method of claim 31, wherein said ring electrode comprises a metal ring, and wherein energizing the ring electrode comprises connecting the metal ring to a high frequency generator.

33. The method of claim 31, wherein the elongate member comprises a flexible catheter having an inflatable balloon on the distal portion, and inserting the distal portion comprises inflating the balloon in the bladder of the patient.

34. The method of claim 31, wherein energizing the ring electrode includes sustaining the energizing for sufficient time to alter tissue in the prostate by temperature elevation to relieve symptoms of urinary obstruction.

\* \* \* \* \*